United States Patent [19]

Olsen

[11] Patent Number: 4,483,874
[45] Date of Patent: Nov. 20, 1984

[54] PREPARATION OF MILK SUBSTITUTE

[75] Inventor: Hans A. S. Olsen, Vanlose, Denmark

[73] Assignee: Novo Industri A/S, Denmark

[21] Appl. No.: 491,184

[22] Filed: May 3, 1983

[30] Foreign Application Priority Data

May 6, 1982 [DK] Denmark .............................. 2025/82

[51] Int. Cl.$^3$ .......................... A23L 1/36; A23B 7/10
[52] U.S. Cl. ....................................... 426/44; 426/52; 426/46
[58] Field of Search ....................... 426/44, 46, 48, 49, 426/52

[56] References Cited

U.S. PATENT DOCUMENTS

| | | | |
|---|---|---|---|
| 2,217,264 | 10/1938 | Weizmann | 426/44 |
| 2,802,738 | 8/1957 | Anson et al. | 426/46 |
| 2,953,456 | 9/1960 | Mohler et al. | 426/46 |
| 3,640,725 | 2/1972 | Sherba et al. | 426/44 |
| 3,761,353 | 9/1973 | Noe et al. | 426/44 |
| 3,846,560 | 11/1974 | Hempenius et al. | 426/44 |

OTHER PUBLICATIONS

Research Disclosure (19314) May 1980, pp. 167–173.

*Primary Examiner*—Raymond Jones
*Assistant Examiner*—Marianne S. Minnick
*Attorney, Agent, or Firm*—Fidelman, Wolffe & Waldron

[57] ABSTRACT

Preparation of a proteinaceous material suited for use in milk substitutes by treatment of crude vegetable proteins such as soy flour, faba bean flour and the like with an SPS-ase preparation. In addition to conversion of the vegetable protein, the treatment hydrolyzes the soluble polysaccharide content in the crude vegetable protein into predominantly mono- and di-saccharides, including dissolving +hydrolyzing previously insoluble polysaccharides.

3 Claims, 1 Drawing Figure

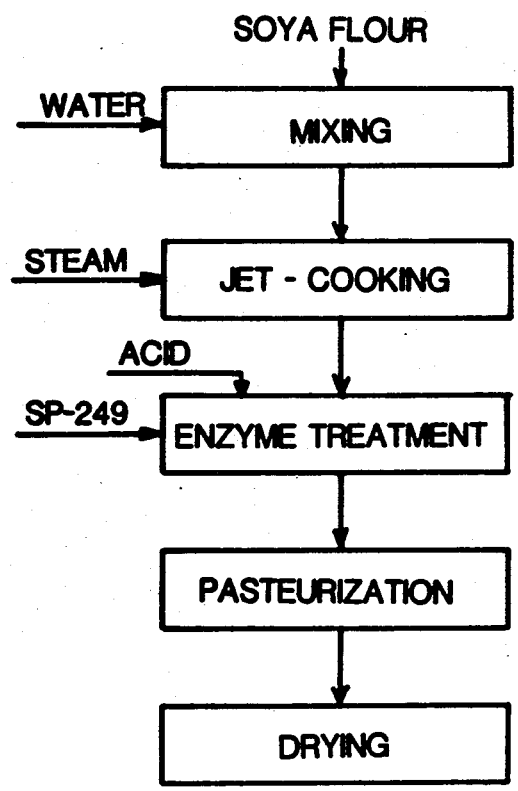

PREPARATION OF MILK SUBSTITUTE

This invention relates to the preparation of milk substitutes, and in particular, to conversion of a vegetable source proteinaceous material such as soy flour or a fullfat soy flour and the like into a protein and carbohydrate step-product capable of emulsifying fats or oils so as to form a milk substitute. The modified protein is largely or entirely water soluble at pH 4.5. The polysaccharides present in the vegetable source proteinaceous material are hydrolyzed with substantial production therefrom of mono- and di-saccharides. Both the step-products and milk substitutes made therewith are believed to be novel.

The basic organic components of milk, particularly bovine milk which is the principle milk in commerce, are protein, butterfat, and milk sugar. To a great extent, comparable but different ingredients can be nutritionally acceptable substitutes for each of the above listed components, if formulated in appropriate proportions into an aqueous emulsion, to wit, a milk substitute. Notwithstanding that milk often is in oversupply, and production thereof is heavily subsidizied domestically, as well as in many foreign countries, a significant potential exists for use of milk substitutes. A body of art is directed to milk substitutes.

One potentially large volume use for a milk substitute is in the dairy industry; calves in large number must be fed either their mother's milk or a milk substitute.

The principal object of this invention is to provide a milk substitute suited to the nutritional needs of young animals, and in particular of calves and piglets.

In the instance of calves, cow's milk is normally available on site, so to speak. A principal determinant for employment of a milk substitute instead of milk is the cost thereof. No dairyman can be expected to pay more for the milk substitute than can be obtained by the dairyman from sale of whole cow's milk. Economics require that milk substitutes intended for animal use be formulated with the least expensive components which, in practice almost always means vegetable source proteins from such protein sources as soy beans, sunflower seeds, cottonseeds, faba beans, field peas, etc. Frequently, use of vegetable source oils and animal fats to replace the butterfat has been proposed. To supply milk sugar, mineral salts and even protein suggestions to employ whey have been made.

By practice of this invention, inexpensive forms of vegetable protein may be converted into a water soluble protein and carbohydrate product suited to preparation of a milk substitute therefrom. The product is soluble or dispersable at pH 4.5. As the art well knows, vegetable proteins are ill-adapted for use in milk substitutes, (see, for example, the discussion posed in U.S. Pat. No. 3,843,828), and must be converted into a proteinaceous substance better adapted to milk substitute purposes. The purity of the vegetable protein to be converted has received attention by the art, as witness the oft repeated comment in U.S. Pat. No. 3,843,828, that an isolated vegetable protein should be employed. The patent describes isolation of protein from soy flakes. Isolation of the protein is required, because the carbohydrate component present in vegetable protein forms such as soy flour, cottonseed meal, faba bean flour, etc. available inexpensively and almost directly from vegetable oil extraction facilities are not considered desirable for inclusion in milk substitutes. For lack of more apt terminology, soy flour and the like are herein termed relatively crude protein forms, to distinguish such forms from the protein isolates recoverable therefrom, containing less polysaccharides per unit weight than the crude form.

Suggestions have been made to hydrolyze the polysaccharides present in relatively crude proteinaceous materials, as for example by the treatment with pectinase taught in U.S. Pat. No. 3,640,723.

Practice of this invention involves concurrent conversion of both protein and polysaccharide in the relatively crude vegetable proteins such as soy flour, faba bean flour, cottonseed meal and the like to form directly products suited for employment as a step-product in production of a milk substitute. The products may be marketed as such in concentrate form for others to employ in production of milk substitutes. Other uses for the products also exist. Soy milk is employed for preparation of tofu, and an improved soy milk can be prepared by practice of this invention.

Mention has been made that the products are characterized by a high degree of water solubility at pH 4.5. Moreover oil in water emulsions formed with the product such as for example a substitute milk are relatively stable at pH 4.5.

THE INVENTION

Briefly stated, this invention comprises treating a relatively crude vegetable protein such as soy flour or fullfat soy flour, faba bean flour and the like, in suspension at pH 4–5, preferably at pH 4.5 with an SPS-ase preparation, preferably the SPS-ase of *Aspergillus aculeatus* CBS 101.43. CBS is Centraalbureau voor Schimmelcultures, Baarn, The Netherlands. With this enzyme it is possible to obtain high product yields and quality products. SPS-ase and the SPS-ase preparations herein preferred are described in detail by U.S. patent application, Ser. No. 334,329, reference thereto being made for full description of this enzyme, and its properties and its preparation from the microorganism source thereof.

DETAILED DISCUSSION OF THE INVENTION

Protein Sources

The usual vegetable protein in relatively crude form available commercially e.g., defatted soy flour, faba bean flour, deoiled cotton seed meal, etc. contain proteins that are not water soluble at their isoelectric points. Practice of this invention converts the vegetable protein into lower molecular weight proteinaceous substances that are more soluble at the isoelectric point of the vegetable protein, and in particular are largely water soluble at pH 4.5.

Practice of this invention is characterized also by capability for converting polysaccharides into the desirable mono- and di-saccharides. A substantial polysaccharide content is present in crude vegetable protein forms such as soy flour, faba bean flour, deoiled cottonseeds, etc. Water insoluble polysaccharides would, of course, be removed by separation following enzymatic conversion of the vegetable protein into a more water soluble proteinaceous substance. However, not all polysaccharides in vegetable protein forms are water insoluble. Absent presence of appropriate carbohydrase activity during the enzymatic digestion, a significant water soluble polysaccharide content accompanies the protein through all dissolution and precipitation steps in the conversion thereof, to appear finally in the milk substitute as an undesired polysaccharide component. Care must be taken so that carbohydrates accompanying the protein are not high in oligosaccharides, since oligosaccharides are known to be responsible for diarrhea and flatulence when given to calves in quantity. It is believed by the inventor hereof that fear of oligosaccharides underlies suggestions to employ vegetable protein isolates for preparation of milk substitute.

The capability for employing the relatively crude forms of vegetable protein in practice of this invention is, of course, an economic advantage. Conversion of crude vegetable proteins with SPS-ase according to practice of this invention converts the protein into a proteinaceous product suited to milk substitute purposes without the expense of first isolating the protein. Moreover, conversion of the polysaccharide content in crude forms of vegetable protein is a separate advantage to practice of this invention. Treatment with SPS-ase hydrolyzes the water soluble polysaccharide content in the crude vegetable protein, and liquefies water insoluble polysaccharides. Such a conversion is consistent with milk substitute purposes. In particular, a proponderance of mono- and disaccharides are produced with oligosaccharides present only in small amounts. In consequence, the polysaccharide content in the crude vegetable protein provides, at least in part, a substitute for the milk sugar component. Less whey or other sugar source need be used.

Preferred relatively crude proteins for practice of this invention are soy flour and faba bean flour.

Comtemplated for practice of this invention is employment of fullfat soy flour, milled dehulled cotton seeds and the like in whole or in part for the protein source. The oil content therein would become part of the conversion product, requiring then less extraneous fat for forming a milk substitute.

SPS-ase

Although reference has been made to the disclosure in U.S. patent application Ser. No. 334,329, filed December 1981, for details of the SPS-ase preparations some discussion here of this enzyme may aid in appreciation of this invention.

The SPS-ase, hydrolyzes SPS, which substance is a water soluble polysaccharide present in crude soy protein and in the protein isolate as well, and it seems in other comparable vegetable source proteins. The SPS-ase preparations contain carbohydrase activites besides SPS-ase as such, notably pectinase, cellulase, and hemicellulase activities. Hydrolysis of SPS is believed to require more than one carbohydrase activity. In addition, a significant proteinase activity is normally present in the SPS-ase preparations. For practice of this invention, the SPS-ase preparation is an all purpose enzyme. It alone can be employed for conversion of soy flour into a proteinaceous substance suited for milk but supplementation may be desirable. If the relatively crude vegetable protein contains a substantial starch content as does faba beans or field peas for example, starch liquefaction by alpha-amylase before, after or along with treatment by SPS-ase is desirable. Addition of some proteinase may sometimes be needed.

Cut-and-try testing on the SPS-ase preparation and with enzyme mixtures is recommended, since each relatively crude vegetable protein commercially available has unique characteristics. In addition, the SPS-ase preparations employed in the relatively small scale studies from which the hereinafter provided Examples are drawn, is not a standardized article of commerce as of the date hereof. Scale-up, both with regard to SPS-ase production by supplier(s) thereof and conditions of its use in large scale practice of this invention, may require some dosage changes from the levels presently believed to be preferred. Such tests may indicate desirability for supplementation by single purpose enzymes e.g., more hemicellulase, amylase, cellulase, proteinase, etc. to achieve optimum results. Supplementation of the SPS-ase preparation is contemplated. Certainly an SPS-ase preparation from a different source microorganism than *Aspergillus aculeatus* CBS 101.43 with the same enzyme activities may be expected to contain the various enzyme activities in somewhat different proportions. All in all, needless losses in product yield and/or in product quality may well be avoided by cut-and-try heating prior to practicing this invention on large scale. Confirmation of the practices herein described by cut-and-try tests and probable variation therefrom is contemplated by the inventor hereof in practice of this invention on large scale.

PROCESS CONSIDERATION

The process of this invention employs a rationale that is believed to be different from that of prior art processes for converting vegetable protein into a proteinaceous substance adapted for milk substitute purposes. For example, prior art processes for forming milk substitutes with vegetable protein employing vegetable protein isolate, the process of U.S. Pat. No. 3,843,828 for one, make little effort to alter the water insolubility of the vegetable protein at its isoelectric point.

In contradistinction to such a practice, the rationale of the present invention is to secure a vegetable protein hydrolysate which is at least largely water soluble balance dispersible or entirely water soluble at the original isoelectric point. For practice of this invention interest is primarily in water solubility and dispersibility in the range of pH 4-5 rather than at the isoelectric point as such. Thus treatment of the crude soy protein with the SPS-ase preparation is at pH 4.0–5.0, preferably at about pH 4.5.

A separate noteworthy aspect to practice of this invention is its considerable concern about liquefaction and hydrolysis of remanence. Pre-treatment of the crude vegetable protein by jet cooking for example, may be advisable and conduct of such a treatment is preferred to improve solubilization of the remanence and of the protein as well Trypsin inhibitors are inactivated.

In the foregoing discussion, the term "milk substitute" has been employed with reference to a material comparable to milk in its contents of protein, fats and sugars. Soy milk which has been proposed as a substitute for milk would not then be a milk substitute within such a context. However, soy milk, as such, can be made by practice of this invention in higher yield than by prior art practices.

Traditionally, soy milk is produced by soaking soy beans in boiling water, wet milling, then extracting with hot water, followed by separation. The liquid phase from the separation is the soy milk. According to practice of this invention, the soy milk is produced by liquefaction of milled soy beans or of soy flour defatted or fullfat by SPS-ase followed by homogenization of the resulting mixture. The soaking step may be eliminated, and/or other enzymes may be included. The optimal reaction parameters for the enzyme reaction for each combination of enzyme and raw material used may be established by cut and try methods, including for example a scan of dosage levels for the particular substrate and enzyme batch with of temperature and reaction time. The temperature should be 25° C.–50° C., preferably at the upper end of this range. It is vital (to obtain the wanted product) that the temperature chosen be sufficiently low to avoid distruction of essential activities in the SPS-ase preparation. Thus the temperature should not exceed 50° C., and somewhat lower operating temperature levels may be required.

The reaction time can be selected in accordance with good manufacturing practice. A suitable range for the reaction time is 2–24 hours, 4–10 hours being preferred.

pH should be in the acid range, preferably pH 4–5, if only because the reaction mixture and product may be microbially protected if pH is below 4.5. Also, the pH of the final milk substitute product is in the same area.

Desirably, the enzyme dosage is chosen for an optimal hydrolysis of proteins which within the context of this invention is a protein product with the best emulsification power. If the degree of hydrolysis of the protein is too low or too high poor emulsification power results. A degree of hydrolysis of about 3–5% of the total peptide bonds has been found to be optimal for emulsification capacity.

The enzymatic treatment of the polysaccharides has to be so thorough that precipitation of polysaccharides does not occur in the final milk substitute for several days.

Desirably, all of the polysaccharides should be sufficiently hydrolyzed to be digestible by the animal. However, it is important that the molecules whether proteins or polysaccharides are not degraded so much that the osmolality of the milk substitute product becomes far greater than is the case in milk. Excessive osmolality in the product is an undesirable characteristic.

To establish optimum operating conditions a dosage response experiment as is provided in example 3 hereinafter may be carried out in laboratory or pilot plant.

Reference is now made to the attached drawing flowsheet showing the conversion of soy flour into a milk substitute ingredient. A final formulation addition of lard, minerals, whey, etc. may be made before final drying or before pasteurization. The SPS-ase treated soy flour is an emulsifier which spontaneously emulsify any fat added in liquid form or melted form. Use of pressure homogenizers are not necessary. A rapid stirrer is enough. For further understanding of this invention, the following Examples of practice thereof are presented. The detailed characteristics of KRF 68, the SPS-ase employed in the examples are provided in S.N. 334,329.

EXAMPLE 1

15 kg of faba bean flour (Farine de Feves from GRANDES MI-NOTERIES A FEVES DE FRANCE, Paris) were suspended in 35 liters of water. 75 g of Termamyl 60 L and 18 g of $CaCl_2$ were added. The suspension was heated to 95° C. using a steam jacketed vessel while stirred. The suspension was then treated at this temperature for sixty (60) minutes. Hereafter pH was adjusted to pH=4.5, and the product was cooled to 50° C. 300 g of the SPS-as preparation KRF 68 was solubilized in one (1) liter of water and added. The reaction was carried out for 440 minutes. [If 10 g of Fungamyl 800 L is included, the liquefied starch component hydrolyzes mainly to disaccharide (maltose).] Thereafter, the reaction mixture was pasteurized at 90° C. for two (2) minutes. An aliquot of the product was then freeze dried and used for stability tests. The sample was then solubilized at ten percent (10%) dry matter, and the solution of the product could be kept stale without sedimentation of days.

An emulsion containing 3.5% oil (soybean oil) formed from solubilized sample was stable without sedimentation for days.

EXAMPLE 2

Soy flour (Sojamel 13) was jet cooked at 150° C. for 25 seconds as described in Example 8 in Ser. No. 334,330 filed Dec. 24, 1981. The jet cooked soy flour was spray-dried and used for the studies described in the following.

Experiment A 50 g of the jet cooked soy flour was mixed with 450 g of water, and pH was adjusted to 4.5 with 4.1 ml 6N HCl. The mixture was then heated to 45° C. in a water bath, and 0.250 g of the SPS-ase preparation KRF-68 was added to the heated mixture which was then reacted for five (5) hours with stirring. Thereafter, the mixture was heat treated at 80° C. for two (2) minutes in order to inactivate the enzyme. For analysis of the results a 100 ml sample was centrifuged at ambient temperature for (15) minutes at $3000 \times g$ (g=gravity). The supernatant was ion-exchanged and analyzed for carbohydrate composition by HPLC. Also, the supernatant was analyzed for Kjeldahl-N and dry matter and the nitrogen solubility index (NSI) and the dry matter solubility index (DSI) was calculated; vide results in Table I. 100 ml of the reaction mixture cooled to 20° C. was poured in a 100 ml graduated glass and kept at 4° C. for two (2) days. The dispersion stability (%) was measured by reading the volume of the dispersions obtained (Table II) after one (1) and two (2) days.

To 200 ml of the reaction mixture (at 20° C.) was added 8 g of soy bean oil. An emulsion was made by blending for two (2) minutes in a Waring Blender. The emulsion stability (%) was measured as above after one and two days.

Experiment B

A reaction was carried out as described above, except that in this case, 1.00 g of the SPS-ase preparation was used. The same analyses and stability measurements described in Section A were performed. Results are shown in Tables I and II.

TABLE I

| | CHEMICAL PROPERTIES OF THE SUPERNATANT | | | | |
|---|---|---|---|---|---|
| Experiments | Enzyme dosage in relation to substrate % w/w | NSI, %* (at pH = 4.5) | DSI, %** (at pH = 4.5) | HPLC results (neutral sugars composition) | |
| A | E/S = 0.5% | 39.9 | 62.4 | $DP_1 + DP_2$ | 79.7% |
| | | | | $DP_3$ | 7.4% |
| | | | | $DP_4$ | 12.2% |
| | | | | $DP_{4+}$ | 8.1% |
| B | E/S = 2.0% | 57.0 | 67.1 | $DP_1 + DP_2$ | 84.4% |
| | | | | $DP_3$ | 6.1% |
| | | | | $DP_4$ | 3.7% |

TABLE I-continued

CHEMICAL PROPERTIES OF THE SUPERNATANT

| Experiments | Enzyme dosage in relation to substrate % w/w | NSI, %* (at pH = 4.5) | DSI, %** (at pH = 4.5) | HPLC results (neutral sugars composition) |
|---|---|---|---|---|
| | | | | DP$_{4+}$ 5.7% |

*NSI = Nitrogen Solubility Index
**DSI = Dry matter Solubility Index

TABLE II

STABILITY TESTS OF THE REACTION MIXTURES

| | Enzyme dosage in relation to substrate % w/w | Stability tests | | | |
|---|---|---|---|---|---|
| | | Without oil | | With oil | |
| Experiments | | Dispersion 1. day | Dispersion 2. day | Emulsion 1. day | Emulsion 2. day |
| A | E/S = 0.5% | 80% | 63% | 100% | 87% |
| B | E/S = 2.0% | 66% | 35% | 85% | 71% |

The data in Tables I and II demonstrate that effects of changing the dosage level of the SPS-ase preparation are not straightforward. Compromise between yield and product characteristics may be required in selection of operating conditions for large scale practice of this invention.

It appears from the chemical analysis of the supernatants that the values for NSI (%) and DSI (%) obtained at the "B" experiment is higher than for the "A" experiment. However, the stability tests carried out on the reaction mixtures show a better value for the "A" samples. Better stability characteristics are probably due to the higher peptide chain length of the proteins in the reaction product mixture formed with the low enzyme dosage.

From the carbohydrate composition measured by HPLC it appears that mainly mono- and disaccharides are produced. Thus, oligosaccharides known to be responsible for diarrhea and flatulence when given to calves in too large amounts are present in small amounts only.

EXAMPLE 3

A dosage response experiment has been carried out in order to demonstrate the control of the enzymatic treatment, and solution of operating parameters.

In each of 5 flask reactors with stirrer and temperature control 100 g of jet cooked soy flour (see example 2) was mixed with 900 g of water. pH was adjusted to 4.5 by means of 5 ml 6N HCl. SPS-ase (KRF-68) was added in the following dosage:

Reactor 1: 0.50% KRF-68 w/w of substitute dry matter
Reactor 2: 0.25% KRF-68 w/w of substitute dry matter
Reactor 3: 0.125% KRF-68 w/w of substitute dry matter
Reactor 4: 0.0625% KRF-68 w/w of substitute dry matter
Reactor 5: 0% KRF-68 w/w of substitute dry matter The reaction was carried out under gentle stirring for 5 hours at 45° C. Hereafter the temperature was raised to 80° C. for 2 minutes in order to inactivate the enzyme. The products were then freeze-dried for later evaluation.

The emulsion stabilities were measured at pH 5.5 by the method described in examples 1 and 2.

HPLC-chromatograms of the sugars showed mono- and di-saccharides increased with dosage. However, the most stable emulsion resulted from the 0.125% dosage, indicating that level to be preferred.

EXAMPLE 4

The soy milk process is illustrated by the following series of enzyme reactions, whereby calculations of the protein solubility index (PSI,%) and the dry matter solubility index (DSI,%) illustrate the yields obtained after separation at pH=7 (vide Table III). The enzyme reactions were carried out under the following conditions:

| | |
|---|---|
| Substrate: | Full fat soy flour (Dansk Sojakagefabrik A/S) |
| Mass of Reaction mixture: | 220 g |
| Mass of substrate: | 20 g |
| Temperature: | 50° C. |
| pH: | 4.5 (6 N HCl) |
| Reaction Time: | Series A: 1 hour |
| | Series B: 0.5–6 hours |
| Enzyme: | SPS-ase (KRF:68) |
| Enzyme dosage: | Series A: E/S-ratio (w/w): 0–8.0% |
| | Series B: E/S-ratio (w/w): 1.0% |

After the reaction pH was adjusted to pH=7 by means of 4N NaOH, and a separation was performed by centrifugation at 3000×g for fifteen (15) minutes.

TABLE III

MASS BALANCE CALCULATIONS IN RELATION TO THE ENZYMATIC SOY MILK PROCESS

| Series | Reaction time hours | Enzyme-dosage E/S % | Reaction mixture | | Supernatant | | Solubility indices | |
|---|---|---|---|---|---|---|---|---|
| | | | % protein | % dry matter | % protein | % dry matter | PSI % | DSI % |
| A | 1.0 | 0 | 3.65 | 8.70 | 1.87 | 5.72 | 49.6 | 63.7 |
| | 1.0 | 0.5 | 3.68 | 8.74 | 2.41 | 6.28 | 63.7 | 70.0 |
| | 1.0 | 1.0 | 3.71 | 8.78 | 2.48 | 6.43 | 65.1 | 71.4 |
| | 1.0 | 2.0 | 3.78 | 8.86 | 2.98 | 7.18 | 77.5 | 79.5 |
| | 1.0 | 4.0 | 3.92 | 9.03 | 3.36 | 7.69 | 84.6 | 83.9 |
| | 1.0 | 8.0 | 4.19 | 9.37 | 3.76 | 8.08 | 88.5 | 85.0 |
| B | 0.5 | 1.0 | 3.64 | 8.78 | 2.39 | 6.41 | 64.0 | 71.1 |
| | 1.0 | 1.0 | 3.64 | 8.78 | 2.56 | 6.60 | 68.7 | 73.4 |
| | 2.0 | 1.0 | 3.63 | 8.78 | 2.79 | 6.91 | 75.2 | 77.1 |
| | 4.0 | 1.0 | 3.63 | 8.78 | 3.10 | 7.29 | 84.0 | 81.7 |
| | 6.0 | 1.0 | 3.63 | 8.78 | 3.39 | 7.69 | 92.3 | 86.5 |

I claim:

1. A method for converting crude forms of vegetable protein into a water-soluble proteinaceous and carbohydrate material characterized by water solubility and dispersibility at pH 4–5 and by a preponderance of mono- and di-saccharides for the carbohydrate content which comprises treating the crude vegetable protein suspended in aqueous medium with an SPS-ase preparation said SPS-ase being characterized as capable of degrading the water-soluble polysaccharide which binds to soy protein.

2. The method of claim 1 which further comprises emulsifying the SPS-ase treated proteinaceous material with a sufficient amount of vegetable oil to form a milk substitute.

3. The method of claim 1 wherein finely divided soy beans or soy flour comprises the crude vegetable protein.

* * * * *